United States Patent
Satoh (10) Patent No.: US 7,195,684 B2
(45) Date of Patent: Mar. 27, 2007

(54) APPARATUS AND METHOD FOR PRODUCING ARTICLE

(75) Inventor: Hitoshi Satoh, Osaka (JP)

(73) Assignee: Zuiko Corporation, Osaka (JP)

( * ) Notice: Subject to any disclaimer, the term of this patent is extended or adjusted under 35 U.S.C. 154(b) by 520 days.

(21) Appl. No.: 10/695,088

(22) Filed: Oct. 28, 2003

(65) Prior Publication Data
US 2004/0089403 A1    May 13, 2004

(30) Foreign Application Priority Data
Nov. 1, 2002    (JP) .............................. 2002-319467

(51) Int. Cl.
*A61F 13/15* (2006.01)
(52) U.S. Cl. ...................... 156/163; 156/161; 156/164; 156/229; 156/494; 156/495
(58) Field of Classification Search ................ 156/161, 156/163, 164, 229, 494, 495, 496
See application file for complete search history.

(56) References Cited

U.S. PATENT DOCUMENTS

| | | | |
|---|---|---|---|
| 4,578,133 A | * | 3/1986 | Oshefsky et al. ........... 156/164 |
| 4,610,751 A | * | 9/1986 | Eschler ........................ 156/517 |
| 4,726,876 A | * | 2/1988 | Tomsovic, Jr. .............. 156/552 |
| 4,925,520 A | * | 5/1990 | Beaudoin et al. ........... 156/494 |
| 4,946,539 A | * | 8/1990 | Ales et al. ................... 156/495 |
| 5,091,039 A | * | 2/1992 | Ujimoto et al. ............. 156/519 |
| 5,716,478 A | * | 2/1998 | Boothe et al. ............... 156/302 |
| 6,689,115 B1 | | 2/2004 | Popp et al. |
| 2003/0010423 A1 | | 1/2003 | Nakakado et al. |
| 2003/0105442 A1 | | 6/2003 | Johnston et al. |

FOREIGN PATENT DOCUMENTS

| | | |
|---|---|---|
| JP | 1-183502 | 7/1989 |
| JP | 1-272803 | 10/1989 |
| JP | 8-197498 | 8/1996 |
| JP | 8-511707 | 12/1996 |
| JP | 64-38377 | 2/1999 |
| JP | 11-503060 | 3/1999 |
| JP | 11-504228 | 4/1999 |
| WO | 95/00094 | 1/1995 |
| WO | 96/31180 | 10/1996 |
| WO | 97/26851 | 7/1997 |

* cited by examiner

*Primary Examiner*—Jeff H. Aftergut
(74) *Attorney, Agent, or Firm*—Renner, Otto, Boisselle & Sklar, LLP (57) ABSTRACT

An apparatus for producing an article having an elastic member, comprises: a stretcher for receiving the elastic member at a low velocity $V_L$ and outputting the elastic member at a medium velocity $V_M$; a carrier including a first pad and a second pad for picking up the elastic member from the stretcher, and a cutter for cutting off the elastic member while carrying the elastic member; and a station for carrying a web at a high velocity $V_h$ and disposing the cut-off elastic member from a pad onto the web. When the elastic member striding over the first pad and the second pad is cut off, an interval between the first pad and the second pad is shortened so as to reduce a shrinking force of a portion of the elastic member between the first pad and the second pad.

19 Claims, 5 Drawing Sheets

APPARATUS AND METHOD FOR PRODUCING ARTICLE

BACKGROUND OF THE INVENTION

1. Field of the Invention

The present invention relates to an apparatus and method for producing an article having an elastic member, such as a sanitary napkin, a disposable diaper, and a disposable pants-type diaper.

2. Description of the Related Art

In a disposable worn article, an elastic member is placed on the sheet surface to form gathers so that the article fits to various parts of the body of the wearer. The elastic member is preferably placed on the sheet surface at as uniform an extension as possible. The extension being significantly non-uniform may result in poor wearability and leakage of bodily fluids.

Conventional apparatuses and methods for producing a worn article fail to ensure a uniformity of the extension of the elastic member (see, for example, Japanese Laid-Open Patent Publication No. 8-197498, and Japanese National Phase PCT Laid-Open Publication Nos. 8-511707, 11-503060 and 11-504228).

SUMMARY OF THE INVENTION

It is therefore an object of the present invention to provide an apparatus for producing an article having an elastic member that is capable of transferring an elastic member onto a web while preventing point-to-point variations in the extension of the elastic member.

One production apparatus of the present invention includes: a stretcher for receiving an elastic member at a low velocity $V_L$ and outputting the elastic member being stretched at a generally constant medium velocity $V_M$; a carrier including a plurality of pads for successively picking up the elastic member from the stretcher while revolving along a predetermined path; a cutter for cutting off the elastic member while the elastic member is carried by the carrier so as to divide the elastic member into pieces each carried on one of the plurality of pads; and a support section for supporting a web (an example of a transfer base member onto which the elastic member is transferred) and allowing the cut-off elastic member to be transferred from the pad onto the web while carrying the web at a generally constant high velocity $V_h$ greater than the medium velocity $V_M$, wherein each pad of the carrier picks up the elastic member from the stretcher at a generally constant velocity $V_2$ greater than the low velocity $V_L$, and each pad transfers the elastic member onto the web at the high velocity $V_h$ greater than the velocity $V_2$.

In one production method of the present invention, after the preceding first pad picks up the elastic member, the following second pad picks up the elastic member. While carrying the elastic member, the first and second pads come closer to each other so that the front end of the second pad comes close to, or into contact with, the rear end of the first pad. In such a state where the rear end of the first pad and the front end of the second pad are close to, or in contact with, each other, the elastic member is cut off by a cutter at a position between the rear end of the first pad and the front end of the second pad. The first pad carries the cut-off elastic member while increasing its velocity to a position where the cut-off elastic member is transferred onto the web. At the transfer position, the cut-off elastic member is transferred onto the web.

In the present invention, the circumferential velocity $V_2$ of one pad of the carrier may be kept generally constant from when the pad starts picking up the elastic member from the stretcher until when the pad completes the pickup operation. In this way, point-to-point variations in the extension of the elastic member are unlikely to occur. The term "extension" as used herein refers to the degree to which the elastic member is stretched by an external force applied thereon, and is generally proportional to the stress occurring in the member.

The circumferential velocity $V_2$ of the pad may be set to a value that is generally equal to the medium velocity $V_M$. In this way, the extension of the elastic member does not change while the elastic member is carried from the stretcher to the carrier, thereby further reducing the variations in the extension of the elastic member. The circumferential velocity of one pad of the carrier may be kept at a generally constant high velocity $V_h$ from when the pad starts handing over the elastic member onto the web until the completion of the hand-over operation. In this way, the extension of the elastic member does not change while the elastic member is moved from the carrier onto the web, thereby further reducing the variations in the extension of the elastic member.

In the present invention, after the preceding pad completely picks up the elastic member at the velocity $V_2$, the circumferential velocity of the preceding pad may decrease so that the front end of the following pad comes close to, or into contact with, the rear end of the preceding pad, in which state the elastic member may be cut off by a cutter into two pieces corresponding to the two pads. In this way, the elastic member can be cut off at a position between the pads, thereby reducing the point-to-point variations in the extension of the elastic member on each pad.

An anvil that is contacted by the blade of the cutter may be provided at the front or rear end of each pad.

One production apparatus of the present invention includes: a stretcher for stretching an elastic member and outputting the stretched elastic member; cutting means for cutting off the stretched elastic member; a carrier having a plurality of pads, including a first pad and a second pad, each being capable of carrying the cut-off elastic member; and a support section for supporting a transfer base member onto which the elastic member carried by the pad is transferred, wherein: after the first pad picks up a continuous elastic member and the continuous elastic member is placed on at least a portion of the second pad, the elastic member is cut off at a position between the first pad and the second pad; the first pad and the second pad are spaced apart from each other by a predetermined distance when the cut-off elastic member is transferred from the first pad onto the transfer base member; and the distance between the first pad and the second pad when the elastic member is cut off by the cutting means is shorter than the predetermined distance therebetween during the transfer operation.

The elastic member of the present invention may be made of a string rubber, a flat rubber, a mesh rubber, a film, or a material containing a thermoplastic elastic member. A material containing a thermoplastic elastic member may be a hot-melt resin. The film may include a plurality of holes or slits.

In the present invention, the elastic member may be cut off by the mechanical means of pressing a blade onto an anvil, or by a light cutter. A light cutter may cut off the elastic member by irradiating the elastic member with infrared rays and/or ultraviolet rays. Alternatively, the elastic member may be cut off by one or more of pressure, heat and ultraviolet rays. Alternatively, the elastic member may be cut off ultrasonically.

Note that the term "worn article" as used herein may include a finished or semi-finished product of a worn article such as a sanitary napkin, a disposable diaper, a disposable pants-type diaper, or a bandage, and may further include a single- or multi-layer sheet product of woven fabric, non-woven fabric, a liquid-permeable or liquid-impermeable sheet material, etc.

DESCRIPTION OF THE PREFERRED EMBODIMENTS

An embodiment of the present invention will now be described with reference to the drawings.

Figure 1A:
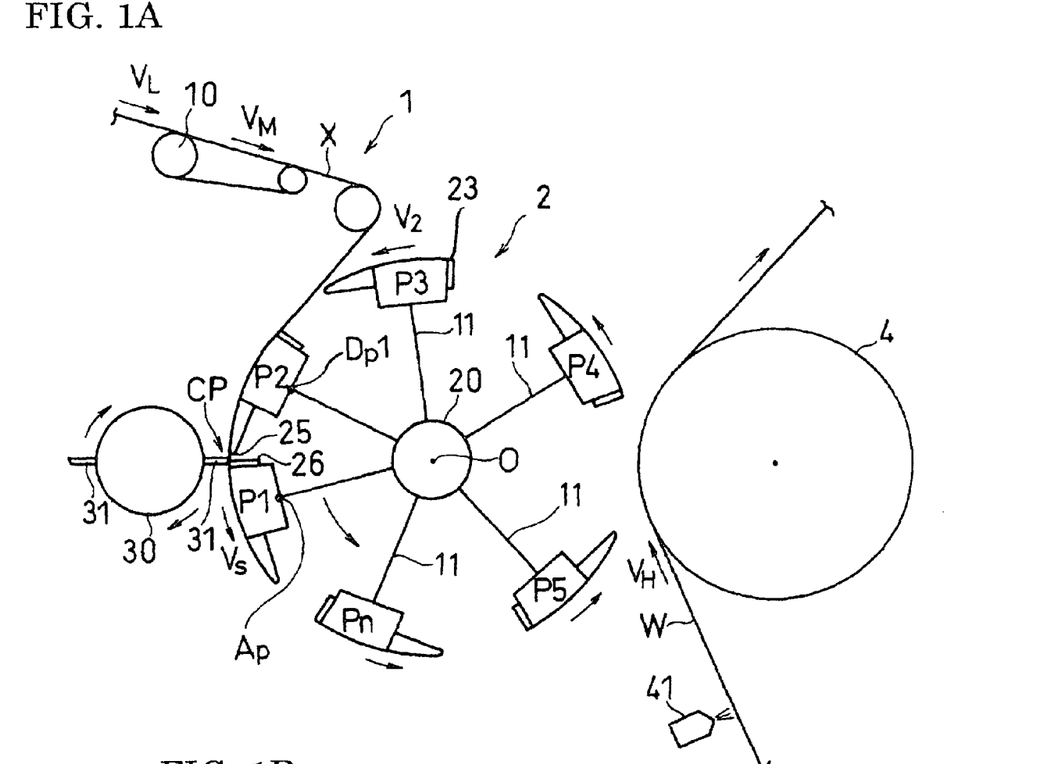
FIG. 1A is a schematic side view illustrating an apparatus for producing a worn article according to an embodiment of the present invention.
Figure 1B:
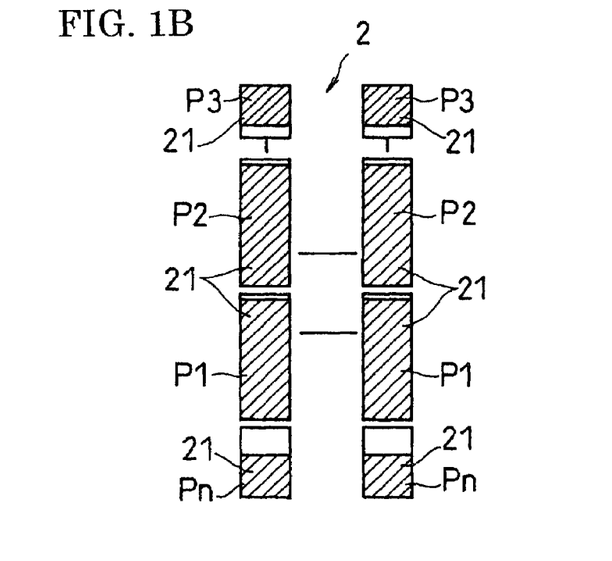
FIG. 1B is a schematic front view illustrating a carrier of the production apparatus.

FIG. 1A and FIG. 1B illustrate a production apparatus of the present invention. The production apparatus illustrated in FIG. 1A and FIG. 1B includes a stretcher 1, a carrier 2 and a disposing station 4.

The stretcher 1 receives an elastic member X, stretches the elastic member X to a predetermined extension, and outputs the stretched elastic member X. The stretcher 1 may include a belt conveyer 10 capable of carrying the elastic member X at a medium velocity $V_M$. The elastic member X is carried from upstream of the belt conveyer 10 at a low velocity $V_L$ lower than the medium velocity $V_M$, and is accelerated to the medium velocity $V_M$ by the belt conveyer 10. Thus, the elastic member X is stretched by the velocity difference.

The carrier 2 includes a plurality of pads P1 for receiving the stretched elastic member X and a cutter 31 for cutting off the elastic member X in a predetermined length. The pads P1 are arranged around a drum 20, and are each connected to the drum 20 via a support rod 11. The pads P1 revolve around the drum (rotor) 20 at a velocity to be described later in a direction indicated by the arrows. For example, the pads P1 may revolve in a circle about the rotation axis O of the drum 20. The arrangement including the drum 20 and the pads P1 may be that of the carrier apparatus disclosed in Japanese Laid-Open Patent Publication No. 63-317576 or Japanese National Phase PCT Laid-Open Publication No. 2000-514024.

A cutter roll 30 includes at least one cutter 31. As the cutter roll 30 rotates, the elastic member X on the pads P1 is cut off. The velocity of the elastic member X on a pad P1 when the elastic member X is cut off is preferably set to be generally equal to the circumferential velocity of the cutter 31. When these velocities are different from each other, the operating lifetime of the cutter 31 may be shortened. Note that if the operating lifetime of the cutter 31 does not have to be taken into consideration, these velocities do not have to be matched with each other.

After the elastic member X is cut off, the interval between adjacent pads P1 and P1+1 is increased, whereby the cut-off pieces of the elastic member X are spaced apart from each other (re-pitched). Each pad P1 is provided with an anvil 23 that is contacted by the cutter 31. The anvil 23 may be provided in a front portion or a rear portion of the pad P1 with respect to the revolution direction Y (see, e.g., FIG. 2A) of the pad P1. In order to appropriately cut off the elastic member X, the anvil 23 is preferably provided in a front end portion 25 or a rear end portion 26 of the pad P1 with respect to the revolution direction Y of the pad P1.

Figures 5A, 5B:
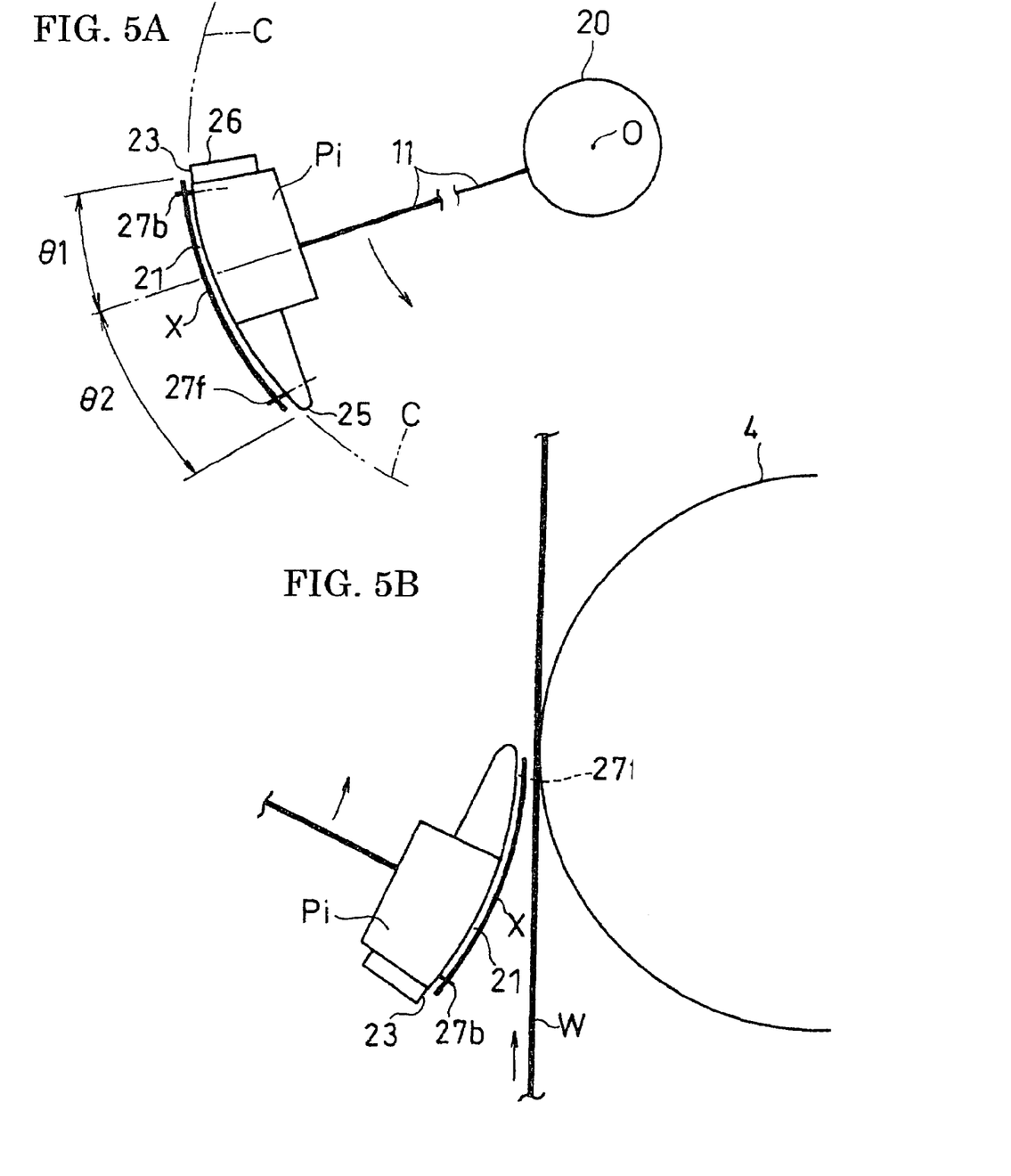
FIG. 5A and FIG. 5B are schematic side views illustrating an alternative way of handing over an elastic member.

For example, referring to FIG. 5A, on the arc C about the rotation axis O, the distance between the anvil 23 and the intersection point between the arc C and the center line of the support rod 11 is set to be shorter than the distance between the end of the pad P1 away from the anvil 23 and the intersection point. In other words, the angle θ1 between the anvil 23 and the center of the support rod 11 about the rotation axis O is set to be smaller than the angle θ2 between the center of the support rod 11 and the front end 25 of the pad P1. When the support rod 11 is positioned as described above, the momentum acting on the support rod 11 when the cutter 31 impacts the anvil 23 is reduced, whereby the durability of the apparatus may be improved.

The production apparatus may include a plurality of carriers 2. For example, FIG. 1B illustrates the carrier 2 including two arrays of pads P1. With such an arrangement, two lines of the elastic member X can be attached to two positions on a web W that are spaced apart from each other by a predetermined interval in the width direction.

The disposing station 4 supports the web W. Each piece of the elastic member X is carried by the pad P1 and transferred onto the web W supported by the disposing station 4. The web W may be carried while being wound around the disposing station 4 (FIG. 1A) or may be carried while being tangential (and in contact) with the disposing station 4 (FIG. 5B). In either case, in order to transfer the elastic member X onto the web W, the elastic member X and the web W are sandwiched and pressed together between the pad P1 and the disposing station 4. Therefore, it is preferred that the circumferential velocity of the disposing station 4 is generally equal to the moving velocity of the web W.

Note that an adhesive is applied in advance on the elastic member X. The application of the adhesive may be done at any point as long as it is before the elastic member X is transferred onto the web W and as long as a sufficient adhesion of the adhesive is maintained. For example, the adhesive may be applied at the stretcher 1.

Note however that when the elastic member X may be made of a urethane foam, and it may be difficult to apply an adhesive directly on a urethane foam because the adhesive easily permeates into the urethane foam, thereby failing to obtain a sufficient adhesion. In view of this, an application apparatus 41 may be provided upstream of the disposing station 4, and an adhesive may be applied intermittently on the web W onto which the elastic member X is to be transferred.

A method for producing an article having the elastic member X will now be described with reference to FIG. 2A and 2B. Note that the anvil 23 is formed at the rear end portion 26 of the pad P1.

In the pickup step, the stretcher 1 receives the elastic member X at the low velocity $V_L$, and outputs the elastic member X at the medium velocity $V_M$ while the elastic member X is stretched to a predetermined extension. The pad P1 (the first pad P1) of the carrier 2 picks up the stretched elastic member X being output at the medium velocity $V_M$ at the pickup position RP.

In order for the first pad P1 to pick up the stretched elastic member X without substantially changing the extension thereof, the first pad P1 preferably moves at the constant pickup velocity $V_2$, which is generally equal to the medium velocity $V_M$, from the start to end of the pickup operation. The first pad P1 moves at the constant pickup velocity $V_2$ over an angle θ corresponding to the length of the first pad P1 in the revolution direction Y thereof, after the front end 25 of the first pad P1 comes into contact with the elastic member X as indicated by a solid line. The relationship between these velocities $V_L$, $V_M$ and $V_2$ is as shown by Expressions (1) and (2) below.

Low velocity $V_L$ < Medium velocity $V_M$ (1)

Medium velocity $V_M$ = Pickup velocity $V_2$ (2)

Figure 4:
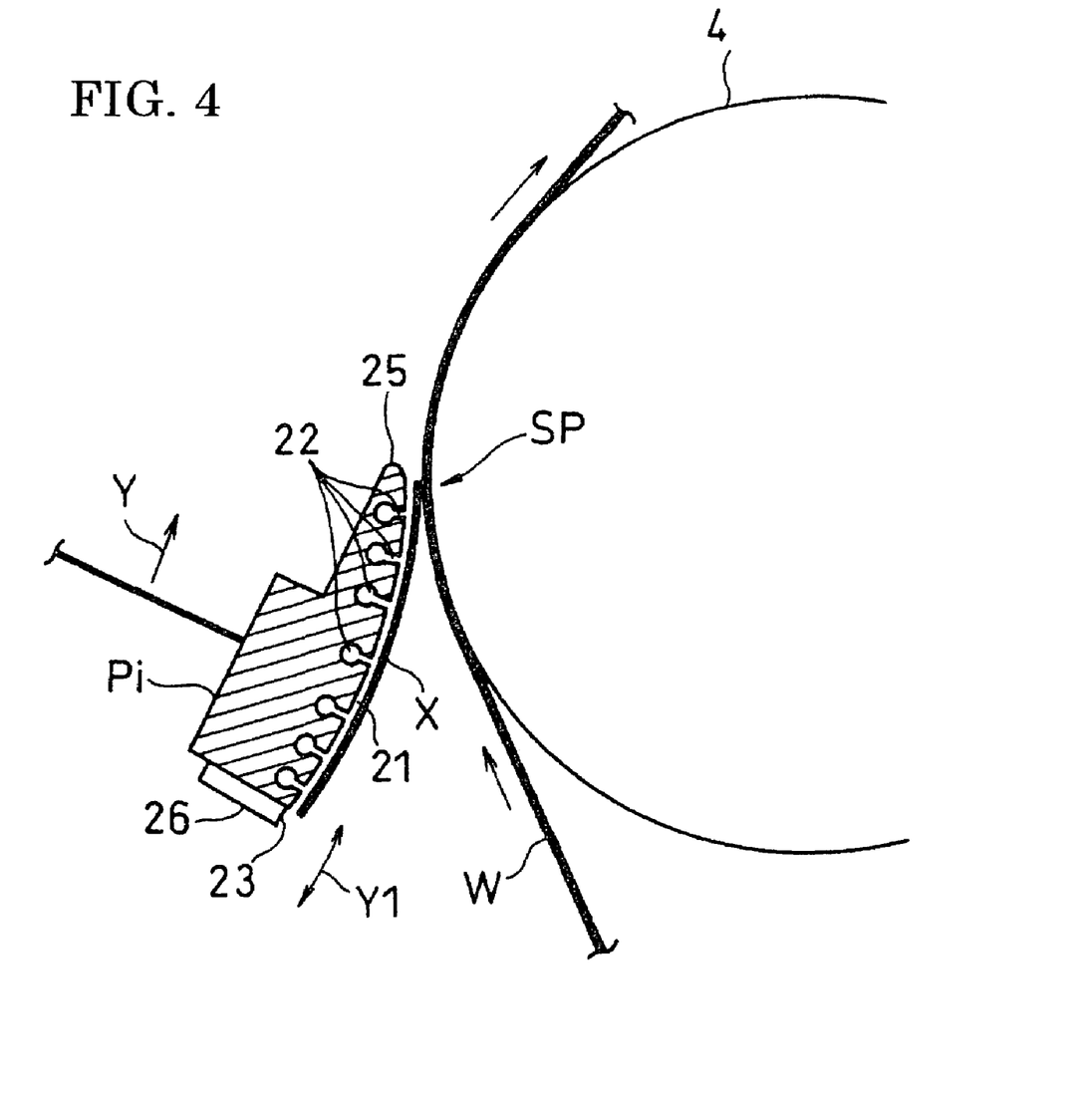
FIG. 4 is a schematic side view illustrating away of handing over an elastic member.

In a case where the elastic member X is picked up by the first pad P1 without slipping thereon, air suction is provided through openings 22 (see, e.g., FIG. 4) of the first pad P1 from slightly before the pickup operation until immediately before the hand-over operation (the hand-over operation will be described later), thereby holding the stretched elastic member X on a holding surface 21 (FIG. 4).

In a case where the elastic member X is picked up by the first pad P1 while slipping thereon, i.e., where the pickup velocity $V_2$ is greater than the medium velocity $V_M$, air suction is provided through the openings 22 of the first pad P1 after the elastic member X is picked up by the first pad P1, thereby holding the stretched elastic member X on the holding surface 21.

Referring again to FIGS. 2A and 2B, in the approaching step, as the first pad P1 reaches the first deceleration starting position Dp1 after the first pad P1 picks up the elastic member X, the first pad P1 moving at the pickup velocity $V_2$ starts decelerating. On the other hand, as illustrated in FIG. 2B, the front end 25 of the following second pad P2 reaches the pickup position RP and starts picking up the elastic member X.

In a case where the elastic member X is picked up by the pad P1 without slipping thereon, the first pad P1 and the second pad P2 move at a generally equal velocity until the second pad P2 completes the pickup operation. Thus, from the start to end of the pickup operation by the second pad P2, the distance (predetermined distance D) between the first pad P1 and the second pad P2 does not substantially change.

In a case where the elastic member X is picked up by the pad P1 while slipping thereon, the initial distance between the first pad P1 and the second pad P2 is greater than the predetermined distance D, and the distance decreases to the predetermined distance D when the second pad P2 completes the pickup operation due to the acceleration of the second pad P2. In either case, upon completion of the pickup operation by the second pad P2, the preceding first pad P1 and the following second pad P2 are spaced apart from each other by the predetermined distance D. Then, the distance between the preceding first pad P1 and the following second pad P2 is shortened before the elastic member X is cut off in the cutting step to be described later. For example, the first pad P1 may be decelerated so that the front end 25 of the following second pad P2 comes closer to the rear end 26 of the first pad P1.

Note that in the approaching step, the second pad P2 may move at a higher velocity than the first pad P1 after the elastic member X is picked up by the second pad P2 while slipping thereon.

In the cutting step, as the rear end 26 of the first pad P1 reaches the cutting position CP, with the distance between the pads P1 and P2 having been shortened, the cutter 31 comes into contact with the anvil 23 at the rear end 26 of the first pad P1, thereby cutting off the elastic member X at a position between the rear end 26 of the first pad P1 and the front end 25 of the second pad P2. Note that the front end 25 of the second pad P2 may be in contact with the rear end 26 of the first pad P1 at the time of cutting.

In the approaching step, a portion Xa of the elastic member X extending between the pads P1 and P2 is slackened as the pads P1 and P2 come closer to each other. Since the elastic member X is cut off by the cutter 31 in the slackened portion Xa in the cutting step, the tension on the elastic member X does not change substantially upon cutting. Thus, it is possible to cut off the elastic member X without changing the tension on the elastic member X that is being held on the pads P1 and P2.

Figures 3A, 3B:
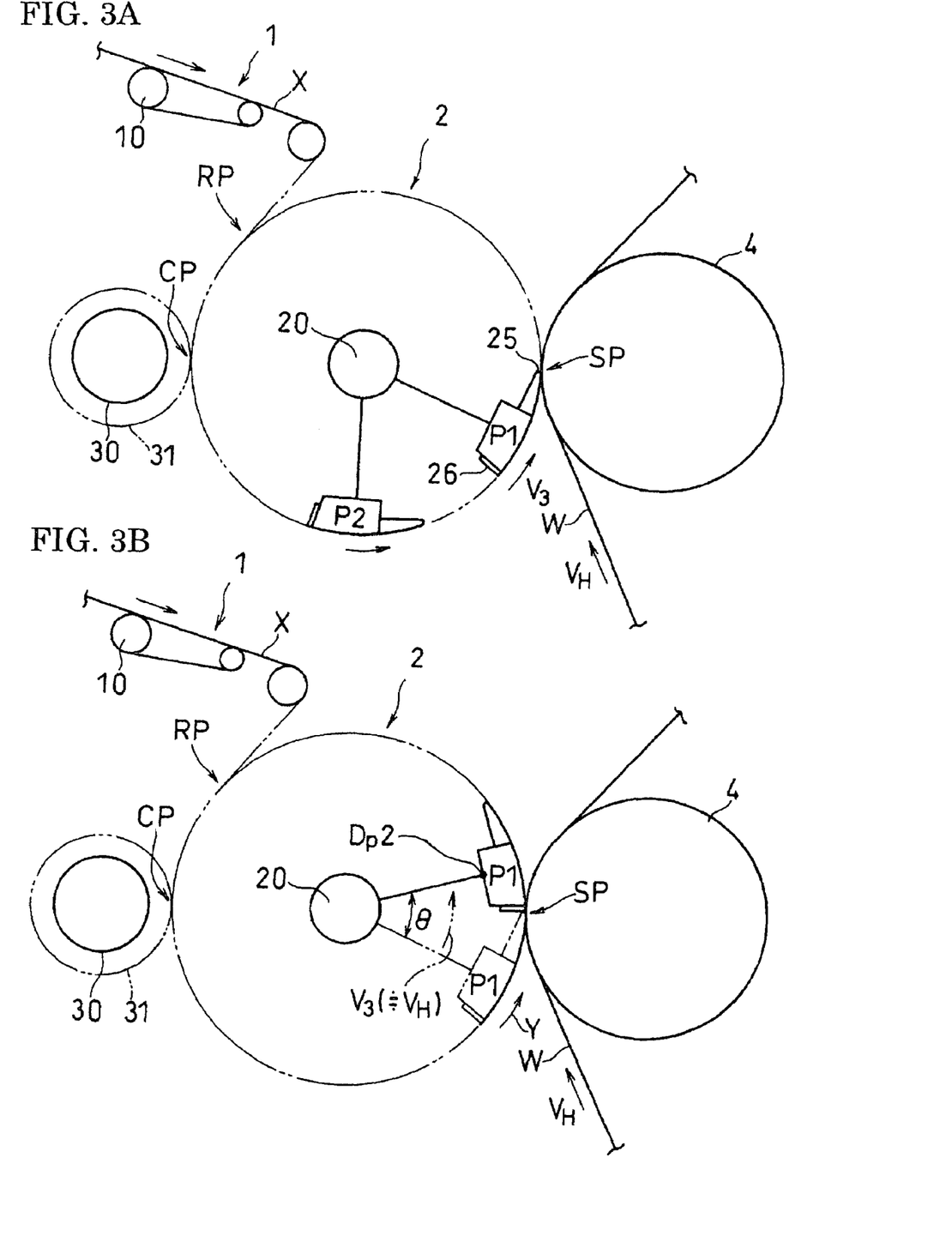
FIG. 3A and FIG. 3B are schematic side views illustrating an apparatus for producing a worn article.

As the first pad P1 reaches the acceleration starting position Ap (FIG. 1A) after the elastic member X is cut off, the first pad P1 is accelerated, thereby increasing the interval between the first pad P1 and the following second pad P2, as illustrated in FIG. 3A (acceleration step).

In the transfer step, the elastic member on the first pad P1 is transferred onto the web W on the disposing station 4 as the first pad P1 passes the hand-over position SP. Before the first pad P1 reaches the hand-over position SP, the air suction through the openings 22 is stopped. Alternatively, the elastic member X on the pad P1 may be pressed and transferred onto the web W on the disposing station 4 by discharging an air through the openings 22 (FIG. 4) successively from the front end 25 to the rear end 26.

In order to transfer the elastic member X onto the web W while the extension of the elastic member X on the first pad P1 illustrated in FIG. 3B is kept generally uniform, the first pad P1 is moved at a constant hand-over velocity $V_3$ and the web W is moved at a constant velocity that is generally equal to the hand-over velocity $V_3$ at least from the start to end of the pickup operation. Therefore, the first pad P1 may be moved at the constant hand-over velocity $V_3$ at least while the first pad P1 is moved over the angle θ corresponding to the length of the first pad P1 in the revolution direction Y thereof, after the front end of the elastic member X on the first pad P1 is pressed against the web W. The hand-over velocity $V_3$ is set to a high velocity $V_h$ that is greater than the pickup velocity $V_2$.

Thus, the pad P1 of the carrier 2 picks up the elastic member X from the stretcher 1 at the generally constant pickup velocity $V_2$ that is greater than the low velocity $V_L$, and transfers the elastic member X onto the web W at the high velocity $V_h$ that is greater than the pickup velocity $V_2$.

Figure 2A:
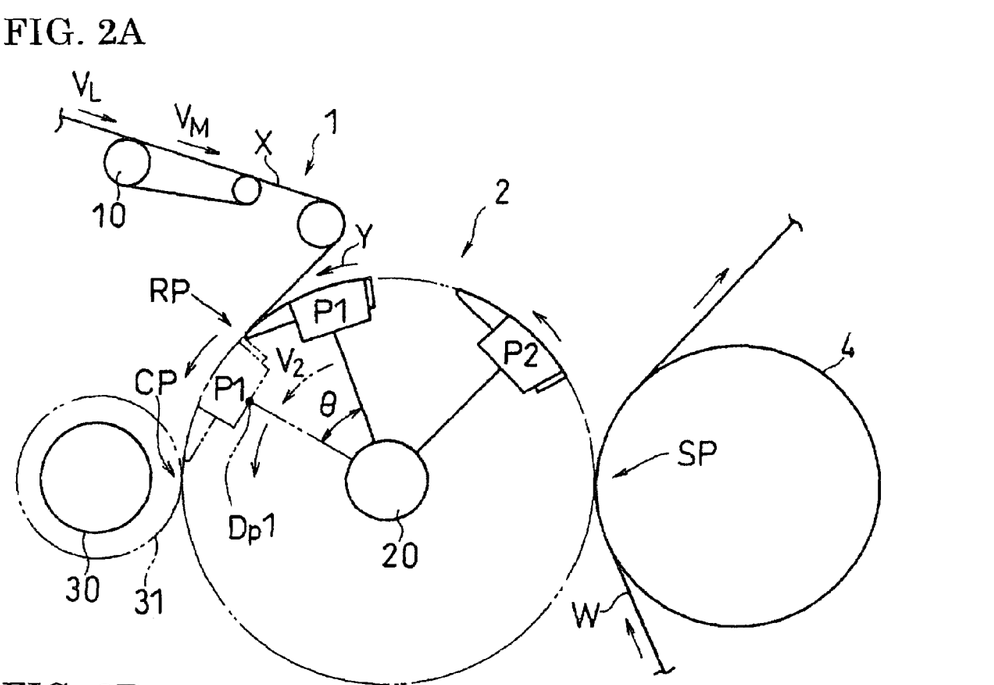
FIG. 2A and FIG. 2B are schematic side views illustrating an apparatus for producing a worn article.
Figure 2B:
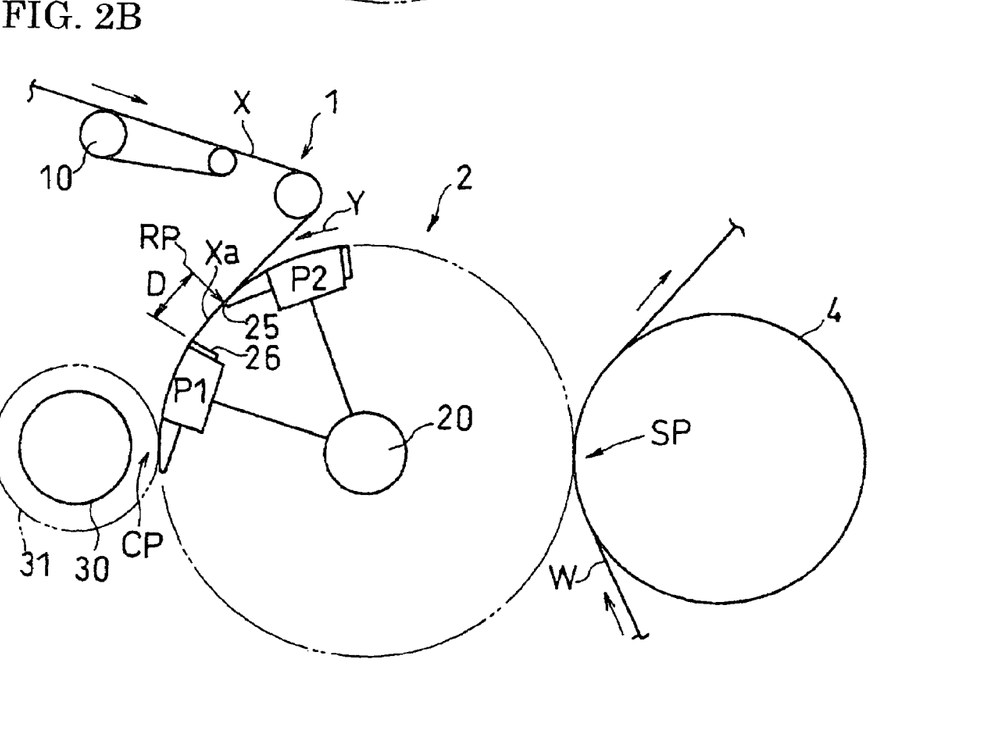

After the hand-over operation, as the first pad P1 reaches the second deceleration starting position Dp2, the first pad P1 starts decelerating, and the velocity of the first pad P1 is reduced to the pickup velocity $V_2$ at least before the first pad P1 reaches the pickup position RP as illustrated in FIG. 2A.

The pad P1 that can be used with the apparatus for producing an article of the present invention will now be described with reference to FIG. 4, FIG. 5A and FIG. 5B.

The pad P1 includes the holding surface 21 capable of holding the elastic member X thereon. The holding surface 21 is an arc-shaped surface extending in the direction Y1 along which the elastic member X is stretched. The holding surface 21 (holding section) may include a plurality of openings 22 to suction the elastic member X onto the holding surface 21. The openings 22 are connected to an air source (not shown). Air is sucked through the openings 22 at a predetermined time so that the elastic member X from the stretcher 1 is held on the holding surface 21 at the pickup as discussed above. Note that in a case where the elastic member X is a member having a smooth surface such as a film, for example, the holding surface 21 may be provided with a smooth surface so that the elastic member X adheres to the holding surface 21.

As the elastic member X is handed over after the cutter 31 cuts off the elastic member X, the air suction through the openings 22 may be released successively from the front end 25 to the rear end 26 of the pad P1. Moreover, as the pad P1 reaches the hand-over position SP, the air suction through the openings 22 may be activated successively from the front end 25 to the rear end 26 so that the elastic member X is gradually transferred onto the web W on the disposing station 4 starting from the front end.

Note that the holding force (suction force) of the holding surface 21 may be greater at the front and rear ends 25 and 26 thereof than in the central portion thereof in the direction Y1 along which the elastic member X is stretched. This is because a greater force for shrinking the elastic member X acts upon the front and rear ends 25 and 26 than on the central portion. The uneven holding force distribution may be provided by, for example, forming more openings 22 at the opposite ends of the pad P1 than in the central portion thereof.

The pad P1 may have the following configuration for holding the elastic member X thereon. For example, in a case where the elastic member X is a member that easily permits air therethrough such as a urethane foam, the elastic member X cannot be held sufficiently only with the air suction. In such a case, the holding surface 21 (holding section) of the pad P1 may have minute irregularities. Such irregularities may be obtained by bonding sandpaper, or the like, on the holding surface 21, or directly cutting the holding surface 21 to form irregularities. Moreover, the holding surface 21 may be made of a rubber material so that the elastic member X will not slip thereon.

Furthermore, the holding section may alternatively be provided in the form of retractable needles 27f and 27b on the holding surface 21 of the pad P1 as shown in FIG. 5A. The needles 27f and 27b are provided at the front end 25 and the rear end 26, respectively, of the first pad P1. The needles 27f and 27b project as illustrated in FIG. 5A when picking up the elastic member X from the stretcher 1 so that they pierce through the elastic member X to hold the stretched elastic member X. In the hand-over operation, the needle 27f retracts first and then the needle 27b retracts, as illustrated in FIG. 5B, to transfer the elastic member X onto the web W.

Note that the pad P1 may be a re-pitching/turning device capable of picking up the elastic member X and then changing the orientation of the elastic member X. In such a case, the holding surface 21 of the pad P1 does not have to be curved in an arc shape, but may alternatively be flat. The carrier apparatus disclosed in EP 1 162 262 A1 may be used as the re-pitching/turning device.

As described above, according to the present invention, an elastic member stretched by a stretcher is picked up by pads, whereby the extension of the elastic member on the pads is unlikely to vary. Thus, the gathers of the obtained product provide a substantially uniform shrinkage across the gathers.

Moreover, the elastic member is cut off into individual pieces each of which is carried on one pad. Therefore, local variations in the extension of the elastic member on each pad are unlikely to occur.

Furthermore, each pad transfers the elastic member onto a web at a high velocity $V_h$ that is greater than a pickup velocity $V_2$, whereby the individual pieces of the elastic member at a predetermined extension can be placed on the web while being spaced apart from one another.

What is claimed is:

1. An apparatus for producing an article having an elastic member, comprising:
    a stretcher for receiving the elastic member at a low velocity $V_L$ and outputting the elastic member at a medium velocity $V_M$ greater than the low velocity $V_L$;
    a carrier including a first pad and a second pad for picking up the elastic member from the stretcher, and a cutter for cutting off the elastic member while carrying the elastic member; and
    a disposing station for carrying a web at a high velocity $V_h$ greater than the medium velocity $V_M$ and transferring the cut-off elastic member from the first pad and the second pad onto the web,
    wherein when the elastic member striding over the first pad and the second pad is cut off, an interval between the first pad and the second pad is shortened so as to reduce a shrinking force of a portion of the elastic member between the first pad and the second pad.

2. An apparatus for producing an article having an elastic member according to claim 1, wherein an anvil used when cutting off the elastic member is provided in a rear portion of each of the first and second pads.

3. An apparatus for producing an article having an elastic member according to claim 1, wherein an anvil used when cutting off the elastic member is provided in a front portion of each of the first and second pads.

4. An apparatus for producing an article having an elastic member according to claim 1, wherein:
    the carrier includes a rotor for revolving the first and second pads about a rotation axis;
    the first and second pads are connected to the rotor each via a support rod;
    in a circle about the rotation axis, a distance between an anvil of the first pad used for cutting of the elastic member and an intersection point between the circle and a center line of the support rod of the first pad is shorter than a distance between the intersection point and one end of the first pad that is away from the anvil of the first pad; and
    a distance between an anvil of the second pad used for cutting the elastic member to an intersection point between the circle and a center line of the support rod of the second pad is shorter than a distance between the intersection point and one end of the second pad that is away from the anvil of the second pad.

5. An apparatus for producing an article having an elastic member according to claim 2, wherein:
    the carrier includes a rotor for revolving the first and second pads about a rotation axis;
    the first and second pads are connected to the rotor each via a support rod;
    in a circle about the rotation axis, a distance between the anvil of the first pad and an intersection point between the circle and a center line of the support rod of the first pad is shorter than a distance between the intersection point and one end of the first pad that is away from the anvil of the first pad; and a distance between the anvil of the second pad to an intersection point between the circle and a center line of the support rod of the second pad is shorter than a distance between the intersection point and one end of the second pad that is away from the anvil of the second pad.

6. An apparatus for producing an article having an elastic member according to claim 3, wherein:
the carrier includes a rotor for revolving the first and second pads about a rotation axis;
the first and second pads are connected to the rotor each via a support rod;
in a circle about the rotation axis, a distance between the anvil of the first pad and an intersection point between the circle and a center line of the support rod of the first pad is shorter than a distance between the intersection point and one end of the first pad that is away from the anvil of the first pad; and
a distance between the anvil of the second pad to an intersection point between the circle and a center line of the support rod of the second pad is shorter than a distance between the intersection point and one end of the second pad that is away from the anvil of the second pad.

7. An apparatus for producing an article having an elastic member according to claim 1, wherein each of the first and second pads includes a plurality of openings.

8. An apparatus for producing an article having an elastic member according to claim 2, wherein each of the first and second pads includes a plurality of openings.

9. An apparatus for producing an article having an elastic member according to claim 3, wherein each of the first and second pads includes a plurality of openings.

10. An apparatus for producing an article having an elastic member according to claim 1, wherein a holding surface of each of the first and second pads is smooth.

11. An apparatus for producing an article having an elastic member according to claim 2, wherein a holding surface of each of the first and second pads is smooth.

12. An apparatus for producing an article having an elastic member according to claim 3, wherein a holding surface of each of the first and second pads is smooth.

13. An apparatus for producing an article having an elastic member according to claim 1, wherein a holding surface of each of the first and second pads has irregularities.

14. An apparatus for producing an article having an elastic member according to claim 2, wherein a holding surface of each of the first and second pads has irregularities.

15. An apparatus for producing an article having an elastic member according to claim 3, wherein a holding surface of each of the first and second pads has irregularities.

16. An apparatus for producing an article having an elastic member according to claim 1, wherein each of the first and second pads includes a retractable needle for holding the elastic member thereon.

17. An apparatus for producing an article having an elastic member according to claim 2, wherein each of the first and second pads includes a retractable needle for holding the elastic member thereon.

18. An apparatus for producing an article having an elastic member according to claim 3, wherein each of the first and second pads includes a retractable needle for holding the elastic member thereon.

19. A method for producing an article, comprising the steps of:
stretching an elastic member;
placing the stretched elastic member successively on a first pad and a second pad;
cutting off the elastic member placed on the first and second pads at a position between the first and second pads; and
disposing the cut-off elastic member onto a web, wherein in the cutting step, the elastic member is cut off after an interval between the first pad and the second pad is shortened.

* * * * *